(12) United States Patent
Hoc et al.

(10) Patent No.: US 12,019,079 B2
(45) Date of Patent: Jun. 25, 2024

(54) NON INVASIVE PROCESS FOR THE EVALUATION OF THE QUALITY OF INTERNAL DENSE CONNECTIVE TISSUES

(71) Applicants: ECOLE CENTRALE DE LYON, Ecully (FR); UNIVERSITE PARIS-SACLAY, Saint Aubin (FR); UNIVERSITE DE PARIS, Paris (FR); ASSISTANCE PUBLIQUE—HOPITAUX DE PARIS, Paris (FR)

(72) Inventors: Thierry Hoc, Charbonnieres les Bains (FR); Jean-Charles Auregan, Paris (FR); Morad Bensidhoum, Sevres (FR); Catherine Bosser, Charbonnieres les Bains (FR); Hassan Zahouani, Besancon (FR)

(73) Assignees: ECOLE CENTRALE DE LYON, Ecully (FR); UNIVERSITE PARIS-SACLAY, Saint Aubin (FR); UNIVERSITÉ DE PARIS, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 864 days.

(21) Appl. No.: 16/966,197

(22) PCT Filed: Sep. 24, 2018

(86) PCT No.: PCT/EP2018/075803
§ 371 (c)(1),
(2) Date: Jul. 30, 2020

(87) PCT Pub. No.: WO2019/149393
PCT Pub. Date: Aug. 8, 2019

(65) Prior Publication Data
US 2021/0041457 A1    Feb. 11, 2021

(30) Foreign Application Priority Data

Feb. 1, 2018  (EP) .................................... 18305107

(51) Int. Cl.
*G01N 33/68* (2006.01)
*G01N 21/88* (2006.01)
*G06T 7/00* (2017.01)

(52) U.S. Cl.
CPC ..... *G01N 33/6893* (2013.01); *G01N 21/8851* (2013.01); *G06T 7/0012* (2013.01);
(Continued)

(58) Field of Classification Search
None
See application file for complete search history.

(56) References Cited

U.S. PATENT DOCUMENTS

2009/0068219 A1* 3/2009 Elie .................... A61K 8/64
514/20.1
2011/0202480 A1  8/2011  Maes et al.
2017/0241985 A1* 8/2017  Lachman .............. G06T 7/0012

FOREIGN PATENT DOCUMENTS

JP    2009005845 A    1/2009
JP    2012501753 A    1/2012
(Continued)

OTHER PUBLICATIONS

Kim, Dai Hyun, et al. "Skin microrelief profiles as a cutaneous aging index." Journal of Electron Microscopy 65.5 (2016): 407-414. (Year: 2016).*

(Continued)

*Primary Examiner* — Samah A Beg
(74) *Attorney, Agent, or Firm* — Panitch Schwarze Belisario & Nadel LLP; Erin M. Dunston

(57) ABSTRACT

The invention relates to a non-invasive process for evaluating the quality of one or more dense connective tissue(s)
(Continued)

A- P19, Stage 1 a) picture at 0°    b) picture at 90°

B- P4, Stage 2 a) picture at 0°    b) picture at 90° in a patient, comprising the following steps: a) Analyzing the profile of the microrelief of a cutaneous replica of a portion of the skin of said patient by at least one of the following step: a1. visually assessing on picture(s) of said cutaneous replica the line shape and the anisotropy of the lines; and/or a2. Determining, on picture(s) of said cutaneous replica, the roughness index of the microrelief with an optical sensor, b) identifying cutaneous replica of "stage 1", representative of healthy skins, and cutaneous replica of "stage 2" representative of altered skins, a cutaneous replica of stage 2 being indicative of low quality of the one or more dense connective tissue(s) in the patients body.

10 Claims, 6 Drawing Sheets

(52) U.S. Cl.
CPC ... *G01N 2021/887* (2013.01); *G01N 2800/10* (2013.01); *G06T 2207/30008* (2013.01)

(56) References Cited

FOREIGN PATENT DOCUMENTS

| JP | 2015047422 | A | 3/2015 |
|---|---|---|---|
| JP | 2015130916 | A | 7/2015 |
| WO | WO-02095475 | A1 | 11/2002 |
| WO | WO-03001268 | A1 | 1/2003 |
| WO | WO-2005122893 | A1 | 12/2005 |
| WO | WO-2010028247 | A2 | 3/2010 |
| WO | WO-2013076579 | A2 | 5/2013 |

OTHER PUBLICATIONS

Murphy, Ruth, et al. "Computer-assisted image analysis of skin surface replicas." British Journal of Dermatology 124.6 (1991): 571-575. (Year: 1991).*

Akazaki, S., et al. "Age-related changes in skin wrinkles assessed by a novel three-dimensional morphometric analysis." British Journal of Dermatology 147.4 (2002): 689-695. (Year: 2002).*

Aurégan et al., *Contra-lateral hip fracture in the elderly: are decreased body mass index and skin thickness predictive factors?*, 41 International Orthopaedics (SICOT) 247-252 (2017).

Bérot et al., *Mechanics of osteoporotic trabecular bone*, 13 Mechanics & Industry 373-380 (2012).

Czekalla et al., *Impact of Body Site, Age, and Gender on the Collagen/Elastin Index by Noninvasive in vivo Vertical Two-Photo Microscopy*, 30 Skin Pharmacology and Physiology 260-267 (Aug. 12, 2017).

Hashimoto, *New methods for surface ultrastructure: Comparative studies of scanning electron microscopy, transmission electron microscopy and replica method*, 13(6) International Journal of Dermatology 357-381 (Nov./Dec. 1974).

International Search Report and Written Opinion issued in corresponding PCT Application No. PCT/EP2018/075803 dated Oct. 18, 2018.

Mazzarello et al., *Analysis of the microtopography of the skin by silicone replicas after repeated exposure to actinic radiation at high altitudes*, 15 European Academy of Dermatology and Venereology 224-228 (2001).

Nardin et al., *Automation of a series of cutaneous topography measurements from silicon rubber replicas*, 8(2) Skin Research and Technology 112-117 (2002).

Sakai et al., *In vivo analysis of human skin anisotropy by polarization-sensitive optical coherence tomography*, 7883(1) Photonic Therapeutics and Diagnostics VII 1-4 (2011).

Sampson et al., *A Method of Replicating Dry or Moist Surfaces for Examination by Light Microscopy*, 191(4791) Nature 932-933 (1961).

Sullivan et al., *Demographic factors in hip fracture incidence and mortality rates in California, 2000-2011*, 11(4) Journal of Orthopaedic Surgery and Research 1-10 (2016).

Tupin et al., *Multiscale Approach to Characterize Mechanical Properties of Tissue Engineered Skin*, 44(9) Annals of Biomedical Engineering 2851-2862 (2016).

Vochteloo et al., *Contralateral hip fractures and other osteoporosis-related fractures in hip fracture patients: incidence and risk factors. An observational cohort study of 1,229 patients*, 132 Arch. Orthop. Trauma Surg. 1191-1197 (2012).

* cited by examiner

A- P19, Stage 1 a) picture at 0°　　　　　　b) picture at 90°

B- P4, Stage 2 a) picture at 0°　　　　　　b) picture at 90°

A)

B)

A

B

A

B

NON INVASIVE PROCESS FOR THE EVALUATION OF THE QUALITY OF INTERNAL DENSE CONNECTIVE TISSUES

CROSS-REFERENCE TO RELATED APPLICATIONS

This application is a U.S. National Stage Application pursuant to 35 U.S.C. § 371 of International Patent Application PCT/EP2018/075803, filed on Sep. 24, 2018, and published as WO 2019/149393 on Aug. 8, 2019, which claims priority to European Patent Application No. 18305107.7, filed on Feb. 1, 2018, all of which are incorporated herein by reference in their entireties for all purposes.

FIELD OF THE INVENTION

The present invention relates to methods and kits for evaluating the quality of internal, dense connective tissues, with a non invasive diagnosis process.

This non-invasive process involves determining parameters of the skin, by assessing cutaneous replica from the patients.

Surprisingly, the inventors have shown that some parameters of the skin are correlated with a low quality of internal, dense connective tissues.

BACKGROUND OF THE INVENTION

Quality and optimal functions of the internal organs in a mammal body evoluate with the age of the body, and under particular circumstances such as diseases, disorders and/or unadequate life habits. As a consequence, the quality of the internal organs is highly variable from an individual to another, even for individuals being of the same age.

Quality of the internal organs in a mammal body is evaluated by numerous techniques such as clinical exam, imaging techniques (ultrasound scan, radiography), detection and quantification of biological markers in the body fluids (blood, lymph, urine, secretions), and tissue analysis from biopsy samples.

Among these diagnosis processes, invasive and non-invasive processes are distinguished. For obvious reasons, non-invasive processes are preferred by patients and clinicians. However, when it comes to internal organs, it might be difficult to obtain informations on the quality and function of an internal organ without obtaining and analyzing a sample of the tissue.

Therefore, non-invasive processes for evaluating the quality of internal tissues in a mammal body are currently under investigation, in order to ease diagnosis of specific conditions related to the quality of internal organs.

More specifically, the concerned internal organs are dense connective tissues, also called dense fibrous tissues, a type of connective tissue comprising fibers of collagen and having a mechanical role in the body. Dense connective tissues comprise in particular bones, rope-like structures such as tendons and ligaments, dermis, sheath and fascias.

In particular, the connective tissues whose quality shall be evaluated are bones. Another example of the connective tissue whose quality shall be evaluated is dermis.

Bone-Related Diseases

Bone tissue (osseous tissue) is a hard tissue, comprising an internal matrix made of ossein, mainly composed of collagen, and various mineral salts. Bone tissue also comprises different types of bone cells: osteoblasts, osteocytes, and osteoclasts.

Osteochondrodysplasia is a general term for a disorder of the development of bone and cartilage. Among the common disorders, one can cite osteomyelitis, osteoporosis, osteopenia, osteomalacia, osteolysis, osteosclerosis, and osteochondritis.

Age-Related Changes in Bones

Bone is a living tissue. As human beings age, the structure of bone changes and they become less dense, and therefore weaker, placing elderly people at risk of breaks from a sudden bump or fall. As a result, the bone fracture incidence is higher in older persons, although important individual variations are observed regarding bone quality.

Bones become less dense for a number of reasons, including:

Hormonal changes—in women, menopause triggers the loss of minerals in bone tissue. In men, the gradual decline in sex hormones leads to the later development of osteoporosis;

Bones lose calcium and other minerals;

Elder persons tend to have an inactive lifestyle.

Pathological conditions related to loss of bone density are designated as osteopenia (mild loss) and osteoporosis (strong loss of bone density). Bones that commonly break include the vertebrae in the spine, the bones of the forearm, and the hip. However, until a broken bone occurs, there are typically no symptoms.

In occidental countries, elderly persons are incitated to follow diagnosis tests for determining their risk of fracture, in particular their risk to sustain a hip fracture, that is the major cause for concern in terms of mortality and morbidity.

Processes to Evaluate the Quality of Bones in an Individual

Typically, after a first fracture, the risk of apparition of another fracture is determined in order to closely follow the patients at risk.

Weakness of the bones is diagnosed by different techniques well known by the man skilled in the art, briefly presented below.

Biomarkers are useful tools for detecting bone degradation. For example, breakdown products from the type-I collagen, an important constituent in bones, can be measured in the blood and/or in the urinary excretion of patients: an increase of these degradation products is indicative of a loss of bone mass, and therefore can serve as a biomarker for osteoporosis.

Conventional radiography also allows the detection of reduced bone mass and pre-osteoporosis. However, radiography is relatively insensitive to detection of early disease and requires a substantial amount of bone loss (about 30%) to be apparent on X-ray images.

To diagnose osteoporosis, the "gold standard" diagnosis technique is the determination of the bone mineral density (BMD).

The most popular method for determining BMD is dual-energy X-ray absorptiometry (DXA or DEXA), a non-invasive test performed in order to measure the mineral content of the bone. The measurements, known as T-scores, determine which category (osteopenia, osteoporosis, or normal) a person falls into. Osteoporosis is diagnosed when the bone mineral density is less than or equal to 2.5 standard deviations below that of a young, healthy adult women reference population.

Although efficient, this technique for diagnosing weakness of the bone presents disadvantages: first, the technique is heavy to implement, since it needs a radiography equipment; secondly, the sensibility of the technique is not reliable for certain types of patients such as men under 50 years of age and premenopausal women.

As people are expected to live longer, bone weakness and the correlated fractures, notably hip fractures, will become more common. (For reference on the hip fractures prevalence, see Vochteloo et al., 2012, and Sullivan et al., 2016).

It is therefore important to identify markers and diagnosis processes that could help to the identification of patients presenting a bone weakness, and preferentially processes that would be non-invasive and easy to implement.

WO 2005/122893 discloses a method for diagnosing bone disease, by detecting changes in the physical or chemical structure of keratinized tissues. In particular, this patent application describes that the hardness of nails in individuals is indicative of osteoporosis.

WO 2013/076579 discloses a method for assessing the risk of bone fracture in an individual, by detecting changes in the physical or chemical structure of keratinized tissues, in particular nails, measured by Raman spectroscopy. In particular the level of sulphur bonding in nails is indicative of the risk of bone fracture.

Recently, Auregan and coworkers (Aurégan et al., 2017) identified biomarkers of the risk of contralateral hip fracture in the elderly: they have shown that a significant decrease of the thickness of the skin in individuals increase their risk to suffer a contralateral hip fracture.

Advantageously, a non-invasive process for evaluating the quality of internal organs would accelerate and simplify the identification of patients presenting a fragility in at least one dense connective tissue, and more particularly would allow the detection of bone weakness in a patient.

Processes to Evaluate the Quality of Dermis in an Individual

The dermis or corium is a layer of skin between the epidermis and the hypodermis, that primarily consists of dense irregular connective tissue, and cushions the body from stress and strain. The dermis forms the mechanical frame of the skin. It is composed of fixed cells (fibroblasts) and mobile cells (blood cells). Between cells, the extracellular matrix (ECM) is mainly composed of collagen fibers and elastin.

The quality of the dermis, and therefore of the skin, is highly related to the quality of the ECM, and in particular to its degradation level.

Recently, studies have established a link between the ageing of the skin and the elastin/collagen ratio in the extracellular matrix of the dermis (Czekalla et al., 2017). This ratio has been demonstrated to be a reliable marker for evaluating the intrinsic ageing of the dermis in an individual, a tissue submitted to important individual variations regarding its quality and evolution over time.

For cosmetic but also therapeutic goals, it is important to identify markers for the detection of ageing and/or weak dermis, in order to evaluate the quality of the skin dermis in individuals. Preferentially, said markers would be determined with non-invasive and easy to implement processes.

SUMMARY OF THE INVENTION

The present invention relates to a non-invasive process for evaluating the quality of one or more dense connective tissue(s) in a patient, comprising the following steps:
a) Analyzing the profile of the microrelief of a cutaneous replica of a portion of the skin of said patient by at least one of the following step:

a1. visually assessing on picture(s) of said cutaneous replica the line shape and the anisotropy of the lines; and/or
a2. determining on picture(s) of said cutaneous replica the roughness index of the microrelief with an optical sensor,
b) identifying cutaneous replica of "stage 1", representative of healthy skins, and cutaneous replica of "stage 2" representative of altered skins,
a cutaneous replica of stage 2 being indicative of low quality of the one or more dense connective tissue(s) in the patient's body.

More specifically, the present invention relates to a non-invasive process for evaluating the quality of bone tissue and/or the quality of dermis.

In particular, the present invention is related to a non-invasive process for determining the risk of occurrence of a contralateral hip fracture in a patient.

The present invention also concerns a diagnostic kit comprising:
means for obtaining a cutaneous replica of a patient, including silicone polymer and a molding apparatus, and
at least two reference pictures of reference cutaneous replica, one being representative of the stage 1 and the other one being representative of the stage 2, such as defined previously.

Patients presenting cutaneous replica with medium SILT values have an average of bone yield stress of almost 14 MPa (A), and a Bone Young's modulus of about 900 MPa (B).

Patient presenting cutaneous replica with extreme SILT values have an average of bone yield stress of about 6 MPa (A) and a Bone Young's modulus of about 400 MPa (B).

Figure 6:
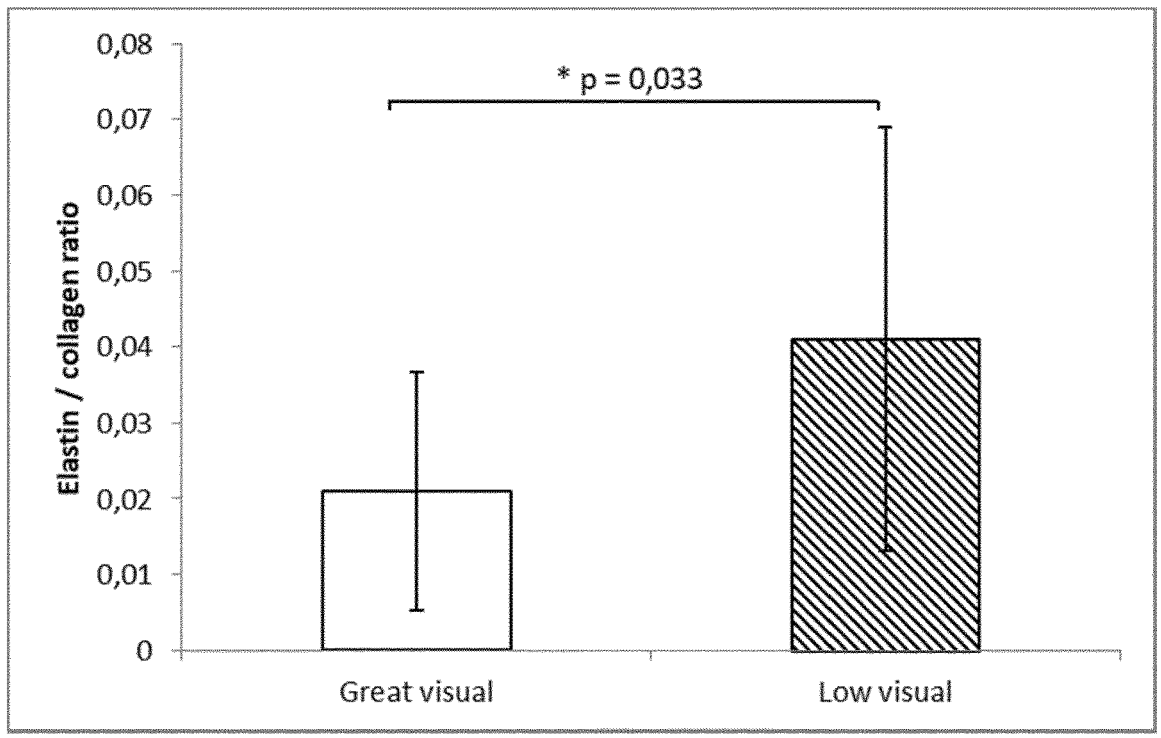
Figure 6:
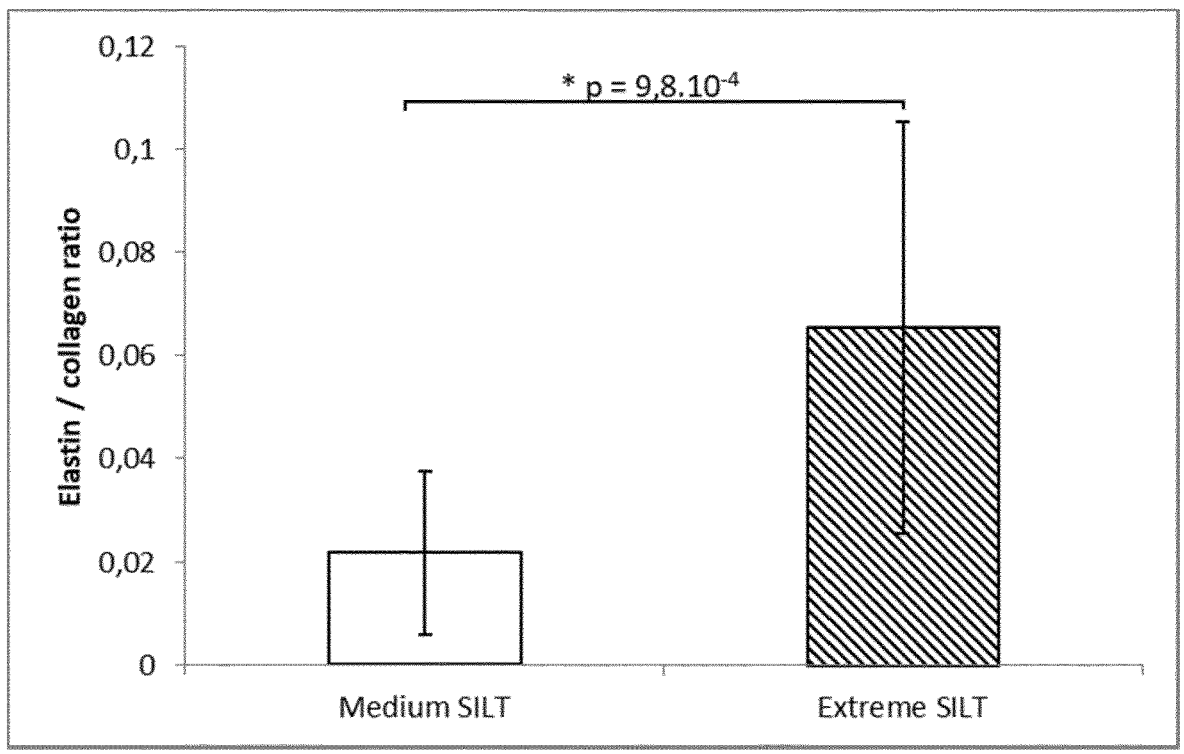

FIG. 6. Application of the process of the invention on the determination of quality of the dermis A) Mean value of Elastin/Collagen ratio for great and low visual groups Patients have been classified in two groups: those presenting cutaneous replica identified as "stage 1" ("great visual") and those presenting cutaneous replica identified as "stage 2" ("low visual"). The corresponding elastin/collagen ratio have been assessed for each patient.

Patients presenting cutaneous replica with a "great visual" have an average of elastin/collagen ratio of 0.021+/−0.016.

Patient presenting cutaneous replica with "low visual" have an average of elastin/collagen ratio of 0.041+/−0.028.

B) Mean value of Elastin/Collagen ratio for medium and extreme SILT groups

Patients have been classified in two groups: those presenting medium values of SILT ("medium SILT") and those presenting extreme values of SILT ("extreme SILT"). The corresponding elastin/collagen ratio have been assessed for each patient.

Patients presenting cutaneous replica with medium SILT values have an average of elastin/collagen ratio of 0.022+/−0.015.

Patient presenting cutaneous replica with extreme SILT values have an average of elastin/collagen ratio of 0.065+/−0.039.

DETAILED DESCRIPTION OF EMBODIMENTS OF THE INVENTION

The present invention relates to a non-invasive process for evaluating the quality of one or more dense connective tissue(s) in a patient, comprising the following steps:
a) Analyzing the profile of the microrelief of a cutaneous replica of a portion of the skin of said patient by at least one of the following step:
   a1. visually assessing on picture(s) of said cutaneous replica: (i) the line shape (continuity/discontinuity), and (ii) the anisotropy of the lines (oriented in multiple directions or not);
   and/or
   a2. determining on picture(s) of said cutaneous replica the roughness index of the microrelief with an optical sensor,
b) identifying cutaneous replica of "stage 1", representative of healthy skins, and cutaneous replica of "stage 2" representative of altered skins,
a cutaneous replica of stage 2 being indicative of low quality of the one or more dense connective tissue(s) in the patient's body.

The term "patient" designates an individual whose quality of at least one internal dense connective tissue has to be evaluated, for any reason, as decided by the man skilled in the art, i.e. a clinician, a physician, a dermatologist, or any health caregiver.

In particular, the patient may be an individual affected by a bone disorder such as osteopenia or osteoporosis. The patient may also be an individual having previously suffered a bone fracture, such as a hip fracture.

The patient may also be an individual affected or susceptible to be affected by a skin disorder, such as dermatitis, psoriasis, unusual peeling, dots, and/or abnormal skin ageing.

In the present application, both terms "patient" and "individual" are used indistinctly.

Since dense connective tissues tend to get of a lesser quality when the individuals age, in a particular embodiment of the invention, the patient is an elderly person.

In the sense of the invention, an elderly person is an individual aged of 70 years or more.

According to the invention, the claimed process is defined as being non-invasive since no break in the skin of the patient is created. Moreover, there is no contact with the mucosa or any internal body cavity.

The process of the invention is performed in vitro on cutaneous replica of the patient, obtained in a non-invasive way.

In the sense of the invention, a "portion of the skin" designates a zone of the skin surface generally unexposed to the sunrays, for example the anterior part of the forearm. The size of this portion of skin may be comprised between 1 cm$^2$ and 15 cm$^2$.

In order to analyze the microrelief of the skin surface, the use of negative replicas made of polymers, that reproduce the microrelief of the skin zone where they polymerized, has been developed by the cosmetic industry. This method is well known by the men skilled in the art, and is notably described in (Sampson, 1961) and (Hashimoto, 1974).

In a specific embodiment of the invention, the cutaneous replica is obtained by application on a portion of the skin surface of the patient of a silicone polymer.

In a preferred embodiment of the invention, silicone replicas are obtained from the anterior part of forearm, on a zone at 5 centimeters distally from the elbow, next to the Flexor Carpi Radialis tendon.

Any molding device and any convenient silicone polymer can be used for creating the silicone molding. Convenient silicon polymers for making the replicas shall polymerize quickly at cutaneous temperature, be sufficiently liquid to fill all the furrows, and avoid deformation in the solidifying process.

In a preferred embodiment of the invention, the used silicone polymer is the commercially available polymer SILFLO®.

Dense Connective Tissues

In the sense of the invention, a dense connective tissue is an internal, fibrous tissue having a mechanical role in the body, comprising fibers mainly composed of collagen. Dense connective tissues comprise in particular bones, rope-like structures such as tendons and ligaments, fascia, sheath, dermis and the hypodermis i.e. the lower layer of the skin.

In a particular embodiment of the invention, the dense connective tissue is bone tissue.

For various reasons, bone quality can be reduced, which generates a higher risk of fracture for the individual. In particular, bone tissues tend to get of a lesser quality when the individuals age. In the human species, bones are more fragile in 70-years-old or more individuals. Other reasons of bone fragility include pathological disorders such as osteopenia and osteoporosis.

According to an embodiment, the process of the invention is adapted for estimating the quality of one or more dense connective tissues mainly composed of collagen fibers, defined as having a content of collagen fibers of at least 50% of the dry weight of the tissue.

For example, dermis is composed of 70% of collagen fibers on a dry weight basis, relatively to the total dry weight of the tissue.

In a particular embodiment of the invention, the dense connective tissue is dermis of the skin.

Changes in the morphology of dermis vary among anatomic location, sex, and age of the individual. Children have relatively thin skin, which progressively thickens until the fourth or fifth decade of life when it begins to thin. This thinning is primarily a dermal change, with loss of elastic fibres, epithelial appendages, and ground substance.

Skin ageing is influenced both by intrinsic and extrinsic factors, and is therefore subject to important individual variations. Determination of an individual's quality of the dermis is an important tool, for various uses as different as diagnostic of skin disorders or adaptation of a cosmetic/hygienic routine for the face.

Evaluation of the Quality of Dense Connective Tissues

The process of the invention is designated to evaluate the quality of one or more dense connective tissue(s) in a patient, by non-invasive means.

In the sense of the invention, it is understood that the process can be used for the evaluation of the quality of one dense connective tissue; or for two, three, four or more dense connectives tissues present in a patient.

In the sense of the invention, the "quality" of a tissue designates its capacity to fulfill its function in the body, for example to resist to mechanical force and/or to carry weight of the body and/or to link different tissues and/or to perform voluntary specific movements.

In the sense of the invention, a "low quality" of a tissue corresponds to a diminished ability for its common function, compared to a reference level of quality, for example compared to the quality of the same tissue in a young and healthy adult.

In particular, a "low quality tissue" present features characteristic of an aged tissue, this ageing being the result of intrinsic or extrinsic factors, and being not systematically linked to the actual age of the individual from whom the tissue belongs.

A "low quality" of a tissue can be observed in individuals presenting a disorder or disease affecting said tissue, or is observed in elderly persons since age tends to diminish the quality of the tissues in a body.

The man skilled in the art knows, for each dense connective tissue, the best and/or the more available technique for characterizing the quality of said tissue.

For example, when the process is implemented for evaluating the quality of bone tissue, common biomarkers allowing to evaluate the quality of bones are:
  the measure of the compressive trabecular bone yield stress, hereafter designed as bone yield stress or BYS, and
  the compressive Young's modulus, hereafter designated as the Young's modulus.

The yield stress is the material property defined as the stress at which a material begins to deform plastically, whereas the yield point is the point where nonlinear deformation begins. Prior to the yield point, the material will deform elastically and will return to its original shape when the applied stress is removed. The yield point determines the limits of performance for mechanical components, since it represents the upper limit to forces that can be applied without permanent deformation. Once the yield point is passed, some fraction of the deformation will be permanent and non-reversible.

In the sense of the present invention, the "bone yield stress" is the stress level wherein, when applied, the bone will deform in a non-reversible way, i.e. will crack under the applied stress. The bone yield stress is expressed in units of pressure (Pascal or MegaPascal).

The man skilled in the art will determine, in function of several biomarkers such as the measured bone yield stress on a sample of bone from a patient, if the bone presents low or good quality.

It is generally admitted that a high bone yield stress is indicative of a good quality of the bone, and that a low bone yield stress is indicative of a low quality of the bone.

Young's modulus, also known as the elastic modulus, is a measure of the stiffness of a solid material. Young's modulus is the ratio of stress to strain (proportional deformation) in a material. Young's modulus is expressed in units of pressure (Pascal or $N/mm^2$ or $kg \cdot m^{-1} \cdot s^{-2}$).

Young's modulus E can be calculated by dividing the tensile stress $\sigma(\varepsilon)$, by the engineering extensional strain, $\varepsilon$, in the elastic portion of the physical stress-strain curve according to the equation (1) below:

$$E \equiv \frac{\sigma(\varepsilon)}{\varepsilon} = \frac{F/A}{\Delta L/L_0} = \frac{FL_0}{A\Delta L} \qquad \text{Equation (1)}$$

where:
E is the Young's modulus;
F is the force exerted on a bone under tension;
A is the actual cross-sectional area, which equals the area of the cross-section perpendicular to the applied force;
$\Delta L$ is the amount by which the length of the bone changes ($\Delta L$ is positive if the material is stretched, and negative when the material is compressed);
$L_0$ is the original length of the bone.

In the sense of the present invention, the "Young's modulus" is the ratio of stress to strain for a sample of bone collected on a patient, as calculated according to the equation (1).

The approximate Young's modulus for human cortical bone is comprised between 7 to 30 GPa, and its median is about 14 GPa (gigaPascal).

It is generally admitted that a high Young's modulus is indicative of a good quality of the trabecular bone, and that a low Young's modulus is indicative of a low quality of the trabecular bone.

According to the sense of the invention, a low quality of the bone corresponds to an increased risk of fracture for the patient, in comparison with the risk of fracture of the general population.

As another example, when the process is implemented for evaluating the quality of dermis, a common biomarker of the quality of dermis is the elastin/collagen (E/C) content in said dermis. Indeed, while collagen fibers thin out during the ageing process, the amorphous elastin fibers accumulate. Therefore, the elastin/collagen ratio tends to increase with the age of the individual and/or is modified under the influence of extrinsic factors inducing ageing phenomena, such as sun exposure.

So far, this E/C ratio was determined from vertical histological sections of invasive biopsies. Recently, non-invasive horizontal scans and vertical two-photon microscopy have allowed the assessment of collagen and elastin content in dermis. Emitted autofluorescence (AF) and second harmonic generation (SHG) signals can be converted into a "SHG-to-AF ageing index of the dermis (SAAID)", an objective parameter for determining the intrinsic and extrinsic ageing of skin.

Analyze of the Cutaneous Replica of the Patients

The process according to the invention comprises a first step of analysis of the profile of the microrelief of a cutaneous replica of a portion of the skin surface of a patient.

In the sense of the invention, the profile of the microrelief designates the "topography" of the cutaneous replica, i.e. the groups of characteristics specific of this non-linear surface, including but not limited to the depth and anisotropy of the lines present in the cutaneous replica. Each profile comprises a sum of specific characteristics that makes it unique.

This profile analysis is performed with pictures of the cutaneous replica.

These pictures are preferentially taken under the following conditions:
with a low-angled, grazing illumination;
said illumination being furnished by at least one optic fiber, preferentially two or more optic fibers.

A low-angled illumination allows highlighting the microrelief of the cutaneous replica, and therefore to obtain a picture wherein the microrelief is visible with the naked eye.

Step a1. Visual Characterization of the Cutaneous Replica

According to a first embodiment of the invention, the step of analyzing the profile of the microrelief of the cutaneous replica consists in visually assessing on picture(s) of said cutaneous replica the line shape and the anisotropy of the lines.

The line shape is defined by the size and continuity of the lines.

Anisotropy is the property of being directionally dependent, as opposed to isotropy. The anisotropy of the lines designates the distribution of the lines along various orientations: are the lines all directed in the same direction, or are they oriented according to multiple directions?

According to a particular embodiment of the invention, this step (a1) comprises the analysis of at least two pictures of the cutaneous replica taken according to different angles.

In a specific embodiment of the invention, two pictures of the cutaneous replica are used for this analysis.

More specifically, these two pictures are taken according to the following angles: at about 0° (first picture) and about 90° (the angle with the first picture).

Figure 1:
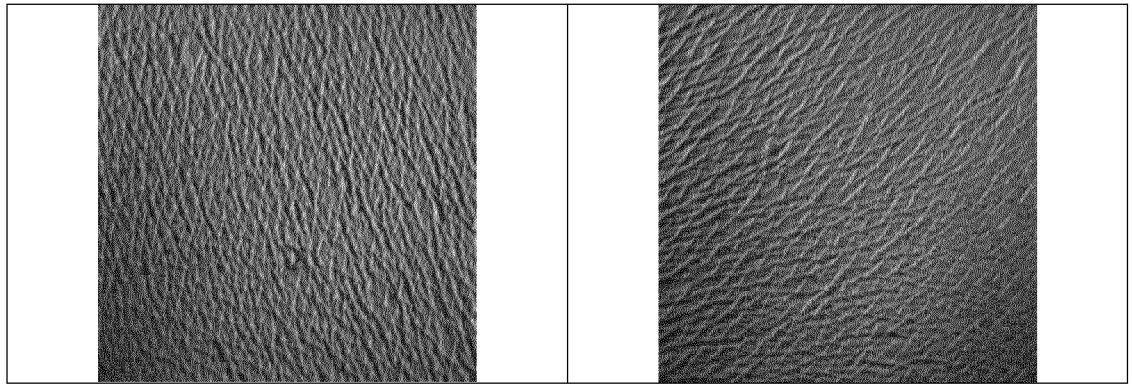
FIG. 1. Reference cutaneous replica pictures:
A) a) Picture at 0° and b) picture at 90°, of the cutaneous replica of the patient P19. These pictures are representative of the stage 1.
B) a) Picture at 0° and b) picture at 90°, of the cutaneous replica of the patient P4. These pictures are representative of the stage 2.
Figure 1:
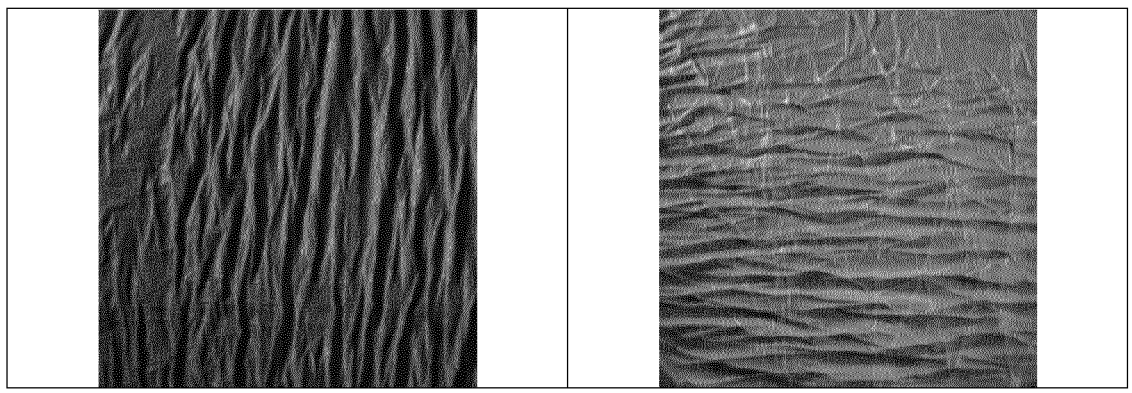

Examples of these pictures are presented in FIG. 1: for each cutaneous replica, from patients P19 and P4, two pictures at 0° and 90° have been taken with a grazing illumination.

Using these pictures, the man skilled in the art is able to discriminate among them two categories of cutaneous replica:
1. cutaneous replica of stage 1; and
2. cutaneous replica of stage 2.

It is understood that several visually-assessable parameters can be used for classifying the cutaneous replica in at least two groups.

In a specific aspect of the invention, the two stages are defined as follow:
a cutaneous replica of stage 1 comprises continuous lines oriented in multiple directions, and
a cutaneous replica of stage 2 comprises short, discontinuous lines mainly oriented in the same direction.

The FIG. 1 illustrates these characteristics of the profiles that are visible with the naked eye, for both stages.

In an advantageous embodiment of the invention, the man skilled in the art uses reference pictures, representative of both stages, to compare with the cutaneous replica to be classified.

Step a2. Quantification of the Roughness Index of the Cutaneous Replica

According to a second embodiment of the invention, the step of analyzing the profile of the microrelief of the cutaneous replica consists in determining the roughness index of the microrelief of the cutaneous replica, using an optical sensor.

An optical sensor converts light rays into an electronic signal. The purpose of an optical sensor is to measure a physical quantity of light and then translates it into a form that is readable by an integrated measuring device, for quantification of the signal.

In the sense of the invention, an optical sensor is a device allowing quantifying the roughness index of a microrelief profile from at least one picture of the uneven surface of a cutaneous replica.

In the sense of the invention, the roughness index (Ra) is defined as the distance of the line at the surface of the replica to the mean line profile. An example of the technique of measure is presented in example 3 and in FIGS. 4A and 4B.

The roughness index can be calculated according to the following equation:

$$Ra = 1/N \Sigma_{i=1}^{N} |Zi| \qquad \text{Equation (2)}$$

where N corresponds to the collected points along the measurement direction, and for each point (i), Zi corresponds to the distance in the vertical direction between the surface of the replica and the mean line profile.

The roughness index is expressed in metric units (μm).

In a specific embodiment of the invention, the roughness index is measured with the optical sensor in two different directions of the replica picture.

In a particular embodiment of the invention, step (a2) comprises the quantification, with an optical sensor, of the roughness index measured in two directions of the replica picture, longitudinal (0°) and transversal (90°).

Each roughness index is called Ra_O and Ra_90, for roughness index measured for each direction at 0° and 90°, respectively.

Skin Index of Living Tissues (SILT)

The Skin Index of Living Tissues (SILT) is defined as a value integrating different parameters measured on the cutaneous replica of a portion of the skin surface.

In particular, the SILT may be defined as the general roughness index of the replica, corresponding to the sum of the values of both roughness indexes measured in each direction 0° and 90°.

It is understood that the process according to the invention can be implemented according to several embodiments, and that the SILT might correspond to another value, such as the sum of three, four or five roughness indexes measured on cutaneous replica. The SILT can be also dependent of other quantifiable parameters of the microrelief of cutaneous replica.

The SILT will then be compared to reference value(s) consistent with its calculation method. Generally, said reference values are the mean or the median of several values determined on several samples obtained from a plurality of patients.

According to a specific embodiment of the invention, the SILT value is compared with at least one reference "cut-off" value. Such "threshold" or "cut-off" reference value can be easily determined by those skilled in the art by means of their general knowledge.

In particular, said SILT may be compared with two reference values defining "median values" and "extreme values" of the SILT. These cut-off reference values are arbitrary values, representative of the "frontiers" between medium and extreme values of SILT measured on several cutaneous replicas.

In this embodiment, a cutaneous replica tested according to the process of the invention will be classified as having a "medium SILT value" when the SILT value measured for this replica is comprised between 45 μm and 120 μm. The limits 45 and 120 μm are comprised into this range.

In this embodiment, a cutaneous replica tested according to the process of the invention will be classified as having an "extreme SILT value" when the SILT value measured for this replica is strictly inferior to 45 μm or is strictly superior to 120 μm.

As presented in the example section, a cohort of 34 patients with hip bone fracture has been assessed for determining the value of SILT of their corresponding cutaneous replica.

Based on the results presented in example 3, it has been concluded that:
- a cutaneous replica of stage 1 is defined as having a medium SILT value, comprised between 45 μm and 120 μm, the limits 45 and 120 μm being comprised into this range; and
- a cutaneous replica of stage 2 is defined as having an extreme SILT value, strictly inferior to 45 μm or strictly superior to 120 μm.

Step (b): Identifying Cutaneous Replica of "Stage 1" or "Stage 2"

According to the process of the invention, each cutaneous replica will be identified as being of "stage 1" or "stage 2".

In a first embodiment of the invention, the step (a1) comprising visually assessing parameters of the lines on the cutaneous replica is performed to identify stage 1 and stage 2 replicas.

In a specific embodiment of the invention, the process for evaluating the quality of a dense connective tissue in a patient consists in both steps (a1) and (b).

In a second embodiment of the invention, the step (a2) comprising determining the roughness index of the microrelief of the replica with an optical sensor is performed to identify stage 1 and stage 2 replicas.

In a specific embodiment of the invention, the process for evaluating the quality of a dense connective tissue in a patient consists in both steps (a2) and (b).

In these embodiments, steps a1 and a2 are implemented independently one of the other.

In a third embodiment of the invention, both steps (a1) and (a2) are performed successively to identify stage 1 and stage 2 replicas. In this case, if results are divergent, the result of step (a2) is considered to be the most reliable and therefore the discrimination between two stages is based on the result obtained with the step (a2).

In another specific embodiment of the invention, the process for evaluating the quality of a dense connective tissue in a patient consists in three steps (a1), (a2) and (b).

Cutaneous replicas of "stage 1" are representative of healthy skins, although cutaneous replicas of "stage 2" are representative of altered skins.

In the sense of the invention, an altered skin presents signs of ageing, with short, discontinuous lines, mainly oriented in the same direction. It is understood that the "skin ageing" phenomena is not directly dependent of the actual age of the individual, but depends also on external factors such as the rate of UV radiations the portion of skin has received, the use of protective creams or not, the intrinsic quality of the skin, the quality of the alimentation, the lifestyle of the individual, etc.

As shown in the examples section, inventors have identified a correlation between the stage of the cutaneous replica and (i) the quality of the bone and (ii) the quality of the dermis, and more generally a correlation between the stage of the cutaneous replica and the quality of any internal dense connective tissue of an individual.

In particular, results show that a cutaneous replica of stage 2 is indicative of low quality of one or more of the dense connective tissues in a patient's body.

Uses of the Non-Invasive Process According to the Invention

The process according to the invention can be used for several applications for various types of patients.

In particular, when the dense connective tissue whose quality is evaluated is bone, the process may be used for determining the risk of occurrence of a contralateral hip fracture in a patient.

In the sense of the invention, a contralateral hip fracture designates a second hip fracture occurring in a patient who had previously undergone a hip fracture of the other leg. It has been shown that the absolute risk of a contralateral hip fracture, after a first hip fracture, is 13.8% (Vochteloo et al., 2012). This risk concerns mainly the elderly persons, the age being a risk factor for a contralateral hip fracture.

The implementation of the process according to the invention would help to determine, among the patients having undergone a first hip fracture, those most at risk for suffering of a contralateral fracture. By determining the stage of their cutaneous replica, it would be possible to discriminate the patients who would need a close follow-up, and those who would not necessitate this follow-up.

More generally, the non-invasive process according to the invention is useful for evaluating a risk of the occurrence of a future fracture. This information is useful to the patient, who may adapt his or her lifestyle, but also to the physician and/or clinician in determining the most effective course of treatment.

This determination of the quality of a dense connective tissue will assist the physician and/or clinician in his choice of preventive and/or therapeutic approach for each patient, in a personalized manner.

In another embodiment of the invention, the process is used for following over time the quality of one or more dense connective tissues in a patient.

In particular in an elderly person, it might be useful to follow over time the quality of the dense connective tissue, in particular of the bones of the patient, in order to adapt his/her lifestyle and in particular his/her level of physic activity.

When the quality of dermis is estimated, the process may be used for determining the risk of occurrence of skin disorders in said individual, and might be useful to adapt the hygienic routine of the individual.

Kit Useful for Performing the Process of the Invention

The invention is also directed to a diagnostic kit comprising:
- means for obtaining a cutaneous replica of a patient, including silicone polymer and a molding apparatus, and
- At least two reference pictures of reference cutaneous replica, one being representative of the stage 1 and the other one being representative of the stage 2, such as defined previously.

For obtaining a cutaneous replica of a patient, as presented previously, the man skilled in the art will use at least the following means: a molding apparatus and a convenient silicon polymer.

In a preferred embodiment of the invention, the used silicone polymer is the commercially available polymer SILFLO®.

In this diagnostic kit, reference pictures representative of the stage 1 and of the stage 2, such as the ones presented in FIG. 1, will be included in order to help the men skilled in the art to discriminate both stages.

Figure 2:
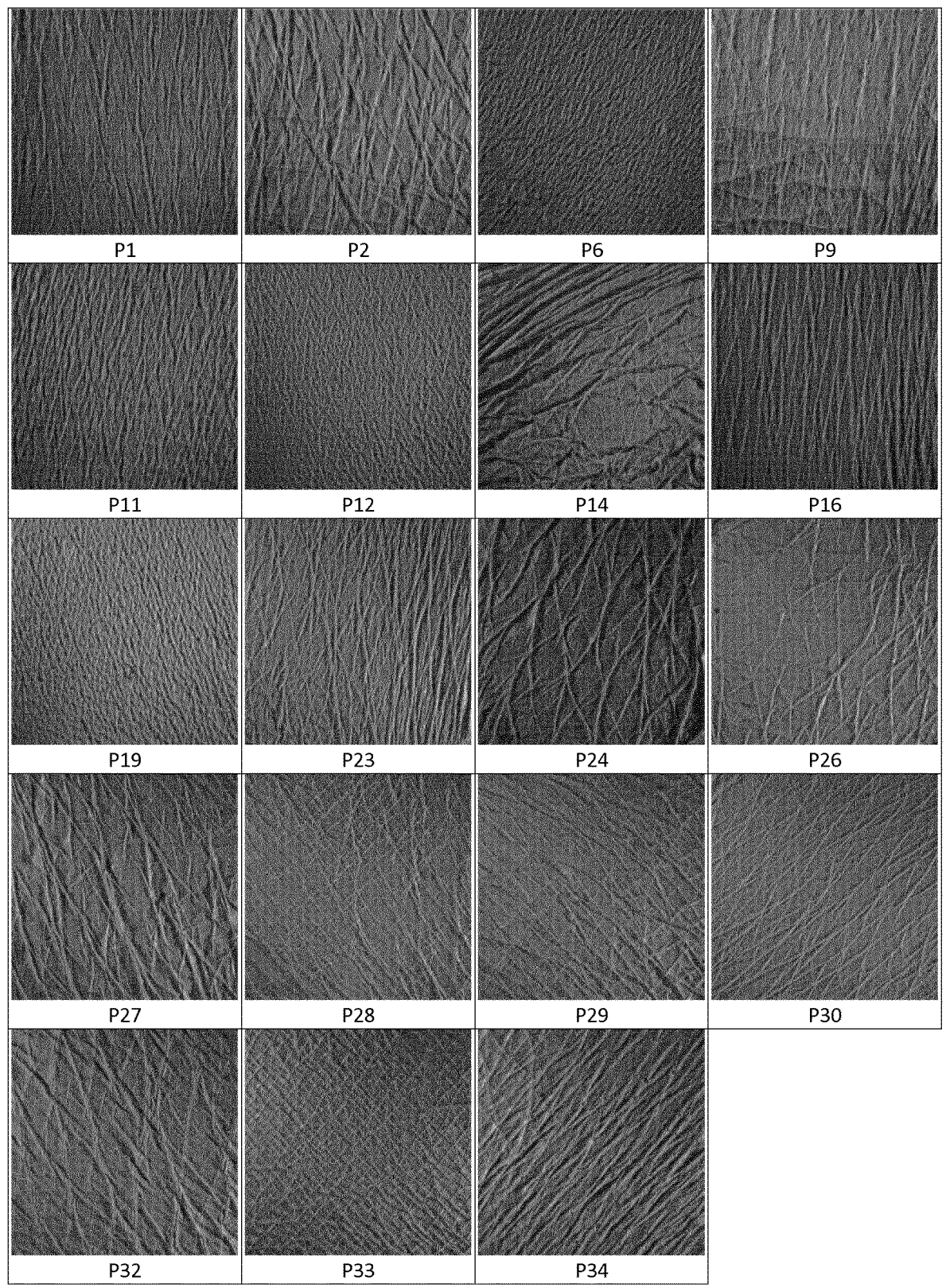
FIG. 2. Pictures of cutaneous replica identified as "stage 1": no alteration of line FIG. 3. Pictures of cutaneous replica identified as "stage 2": clear alteration of line FIG. 4. Quantitative measures with optical sensor
A) Representation of the measurement lines on a replica picture, along the longitudinal direction in solid line, and along the transversal (at 90° of the longitudinal) direction in dotted line.
B) Example of measure of the roughness index of a microrelief: measure on the replica picture of patient P16:
in the longitudinal direction (upper graph), and
in the transversal direction (bottom graph).
Figure 3:
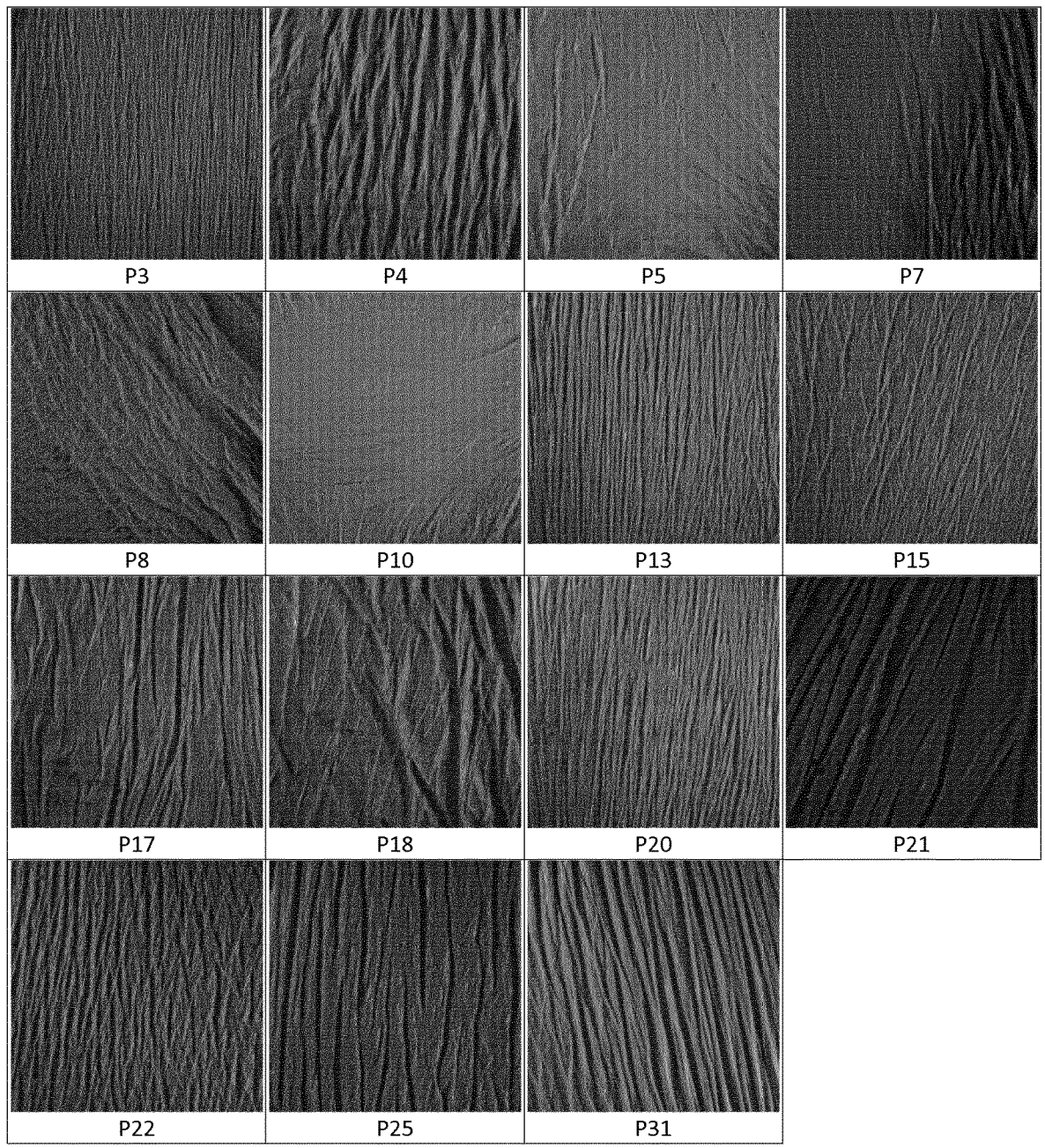

Preferentially, several reference pictures representative of the stage 1 and of the stage 2, such as the ones presented in FIGS. 2 and 3, will be included in the kit.

The invention is also directed to the use of said diagnostic kit, along with a camera and optic fibers, for performing the process according to the invention.

The camera will be used for taking the pictures. Any camera can be used, in particular camera included in smartphones are convenient for implementing the process according to the invention in an easy and convenient way.

At least one optic fiber will be used for illuminating the cutaneous replica, with a grazing light, in order to highlight the lines.

Preferentially, two or more optic fibers shall be used for illuminating the cutaneous replica for taking the picture(s).

According to this embodiment, the evaluation of the quality of a dense connective tissue, such as a bone tissue and dermis, would be realized in less than a day, in a non-invasive way, with minimal equipment.

EXAMPLES

The following examples are for illustration only and are not limiting in any way the invention previously described.

Example 1. Preparation of Cutaneous Replica of the Skin of the Forearm 34 patients having suffered a non-pathologic femoral neck fracture, aged of 50 years or more, without any other medical history, have been included in the clinical study. The mean age was 79.4 years. The mean size was 164 cm and the mean weight 63.5 kg. They are denominated hereafter P1 to P34.

The aim of the clinical study was to identify, if any, a relation between the skin surface microrelief and the quality of the hip bones, and therefore evaluating the risk of occurrence of a contralateral fracture of the hip.

Silicone replicas were obtained from the anterior part of forearm, on a zone at 5 centimeters distally from the elbow, next to the Flexor Carpi Radialis tendon. A specific device was used for the silicone molding. The silicone polymer is SILFLO®, obtained from Monaderm, Monaco.

Pictures of the replicas have been obtained for the qualitative analysis of said cutaneous replicas.

It is essential to take the pictures with a grazing (low-angle) illumination of the replica, with at least one optic fiber, preferentially two optic fibers, to highlight the microrelief of said cutaneous replica.

Two complementary pictures are taken:
  One in the longitudinal direction (direction of the replica along the brachio-radialis muscle), called hereafter "picture at 0°";
  The other one at an angle of 90° from the longitudinal axis, called hereafter "picture at 90°".

In addition, surface of the replica was quantified using optical sensor (pen), from the STIL Company (France). This optical pen is described in patent applications WO 02/095475 and WO 03/001268. The pen measures the distance between the surface of the replica and the objective lens along a line of 10 mm with a vertical resolution of 50 nm and a vertical measurement range of 1.4 mm.

Example 2. Qualitative Classification of Cutaneous Replica by Visualization, and Application on the Determination of the Bone Quality Using both pictures at 0° and 90°, it is possible to classify visually cutaneous replicas in two groups designated as:
  Cutaneous microrelief comprising continuous lines, oriented in multiple directions, are classified as being of "stage 1";
  Cutaneous microrelief comprising short and discontinuous lines, mainly oriented in the same direction, are classified as being "stage 2".

An example for both stage 1 and stage 2 is given on FIG. 1 for patients P4 and P19. As shown in this figure, differences between stages 1 and 2 are visible with the naked eye, since microreliefs of stages 1 and 2 present distinct anisotropy and line shape.

Stage 1 is representative of healthy skins, and stage 2 is representative of altered skins; this last stage is correlated with the natural ageing of the skin and its components.

Pictures of cutaneous replicas from the 34 patients included in the study have been classified between stages 1 and 2. For visualization, all pictures at 0 degree are given on FIG. 2 and FIG. 3.

19 replica have been identified as 'stage 1' (FIG. 2);
15 replicas have been identified as 'stage 2' (FIG. 3).

From these two cohorts, replica P8 and P14 are spatially heterogeneous and are eliminated for the further qualitative analyses.

Application of this Qualitative Classification of the Replica to the Determination of Bone Quality:

In parallel of the classification of cutaneous replicas, the quality of the femoral head of each patient was explored.

Indeed, after the fracture, the explanted femoral head had been conserved to be tested with a validated protocol (Berot et al., 2012).

The mineral density of this femoral head was calculated (C Tan, Bruker MicroCT, Kontich Belgium) and, with a sample of the prelevated sample bone, the limit of the resistance of the bone tissue (bone yield stress) was determined with mechanical tests of monitored compression using the device INSTRON Electropuls 10.000 (Instron World, Norwood, USA).

Then a mean of the bone yield stress was calculated for both groups previously determined in function of the stage of the skin surface microrelief:
  For stage 1 patients, the average bone yield stress value is 13.6+/−4.7 MPa;
  For stage 2 patients, the average bone yield stress value is 8.9+/−4.6 MPa.

The difference in bone yield stress between these two stages, according to the statistical test of Mann-Withney, is significant (p value=0.02).

Example 3. Technique for the Quantitative Classification of Cutaneous Replica, and Application on the Determination of the Bone Quality In order to quantify the differences between both stages, and therefore to classify with more details the replicas, a quantitative technique based on the use of an optical sensor was developed. A measurement of the microrelief of each replica picture was realized on a distance of 10 mm, in the longitudinal direction (0°) and the transversal direction (90°) (see FIG. 4A).

Figure 4:
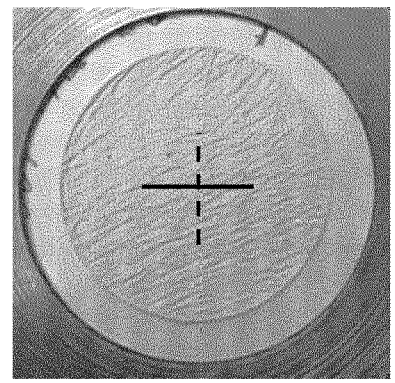
Figure 4:
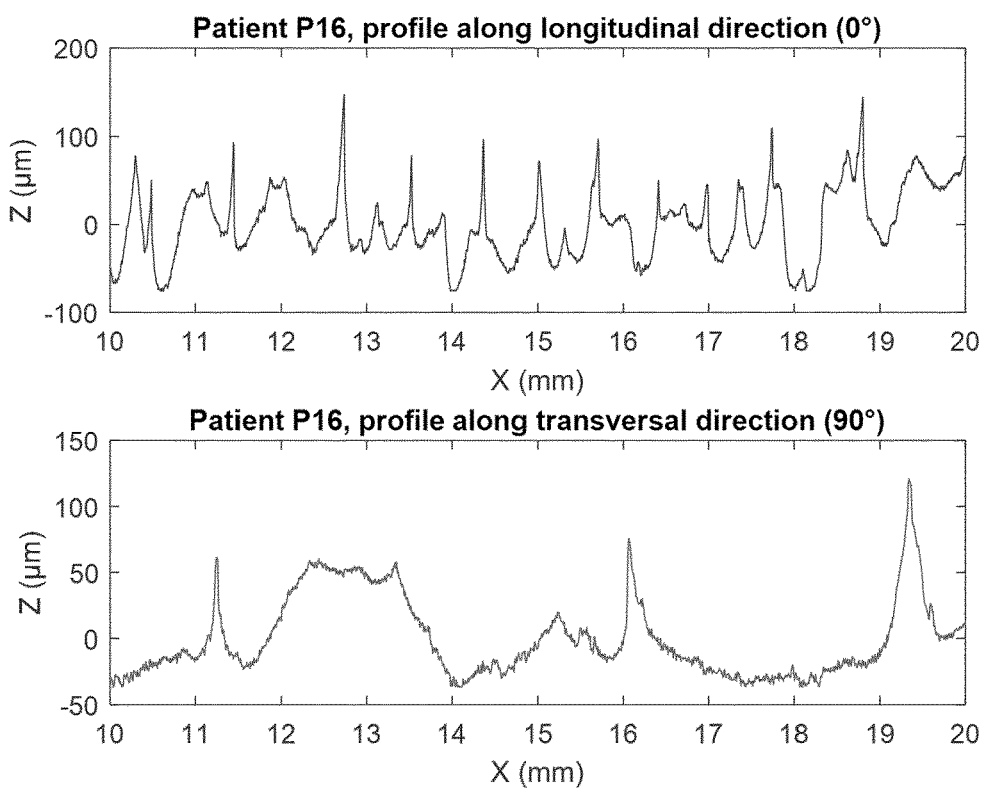

An example of the microrelief obtained by this technique, characterized by the roughness indexes measured in both directions, is presented in FIG. 4B: the cutaneous replica no 16 was assessed as presented above.

On each roughness profile, x is the distance along the line at the surface of the replica. For each x-value, z corresponds to the distance in the vertical direction between the point at the surface of the replica and the mean line profile.

From this picture, the number of peaks in the longitudinal direction (Nb_0) and in the transversal direction (Nb_90) can be determined: these numbers give information about the lines shape in each direction.

Based on these profiles, the roughness index is calculated according to the following equation:

$$Ra = \frac{1}{N}\Sigma_{i=1}^{N}|Zi| \quad \text{Equation 2}$$

wherein N corresponds to the collected points along the measurement direction, and for each point (i), Zi corresponds to the distance in the vertical direction between the surface of the replica and the mean line profile.

This calcul is computed for each direction at 0° and at 90° and results are designated as Ra_0 and Ra_90, respectively. The sum of these two terms is defined as the SILT which represent the general roughness of the replica:

SILT=$Ra\_0+Ra\_90$     Equation 3

The table 1 below gives the value of SILT calculated for each patient P1 to P34:

TABLE 1

Calculated SILT for each patient - compared to the stage defined visually, and values of bone yield stress

| Patient | SILT | Stage (according to SILT value) | Stage (visual) | Correlation visual/SILT | Bone yield stress (MPa) |
|---|---|---|---|---|---|
| P1 | 64 | 1 | 1 | YES | 12.5 |
| P2 | 82 | 1 | 1 | YES | 6.3 |
| P3 | 42 | 2 | 2 | YES | 1.5 |
| P4 | 121 | 2 | 2 | YES | 7.6 |
| P5 | 37 | 2 | 2 | YES | 5.3 |
| P6 | 60 | 1 | 1 | YES | 13 |
| P7 | 66 | 1 | 2 | NO | 15.5 |
| P8 | 117 | 1 | Not done | | |
| P9 | 77 | 1 | 1 | YES | 18.5 |
| P10 | 31 | 2 | 2 | YES | 1.3 |
| P11 | 54 | 1 | 1 | YES | 11.5 |
| P12 | 70 | 1 | 1 | YES | 25.4 |
| P13 | 69 | 1 | 2 | NO | 14.6 |
| P14 | 167 | 2 | Not done | | |
| P15 | 70 | 1 | 2 | NO | 11.9 |
| P16 | 56 | 1 | 1 | YES | 14.8 |
| P17 | 131 | 2 | 2 | YES | 6.2 |
| P18 | 248 | 2 | 2 | YES | 7.5 |
| P19 | 52 | 1 | 1 | YES | 19.7 |
| P20 | 67 | 1 | 2 | NO | 12.1 |
| P21 | 129 | 2 | 2 | YES | 13.5 |
| P22 | 93 | 1 | 2 | NO | 6.2 |
| P23 | 45 | 1 | 1 | YES | 9.7 |
| P24 | 97 | 1 | 1 | YES | 9.1 |
| P25 | 157 | 2 | 2 | YES | 6.7 |
| P26 | 57 | 1 | 1 | YES | 13 |
| P27 | 114 | 1 | 1 | YES | 14 |
| P28 | 58 | 1 | 1 | YES | 17 |
| P29 | 118 | 1 | 1 | YES | 10.6 |
| P30 | 49 | 1 | 1 | YES | 7.7 |
| P31 | 117 | 1 | 2 | NO | 15 |
| P32 | 92 | 1 | 1 | YES | 12.5 |
| P33 | 67 | 1 | 1 | YES | 12 |
| P34 | 74 | 1 | 1 | YES | 17.8 |

Using SILT values, replicas were separated in two groups designated as:

Group "stage 1" corresponds to medium SILT values: values are comprised between 45 µm and 120 µm, or are equal to 45 µm or 120 µm (120≥SILT≥45 µm).

Group "stage 2" corresponds to extreme SILT values: strictly lesser than 45 µm or greater than 120 µm.

Among the 32 fully evaluated patients, 6 patients (P7, P13, P15, P20, P22, P31) replica were classified visually as being of «stage 2» i.e. having an altered skin. However, after the calculation of the SILT of these replica, and comparison with the reference values defined as above, these patients were re-classified in the group "stage 1".

Interestingly, the incorrect visual classification (stage 2 instead of stage 1) leads to a positive re-qualification of the patients, who were finally classified as being "stage 1" after determining the roughness index of the microrelief of their cutaneous replica.

Compressive bone yield stress values are given for comparison, because this parameter is usually considered as one of good biomarker of the bone quality; however, this measure shall not be considered, by itself, as giving a definitive opinion on the quality of the bone.

Figure 5:
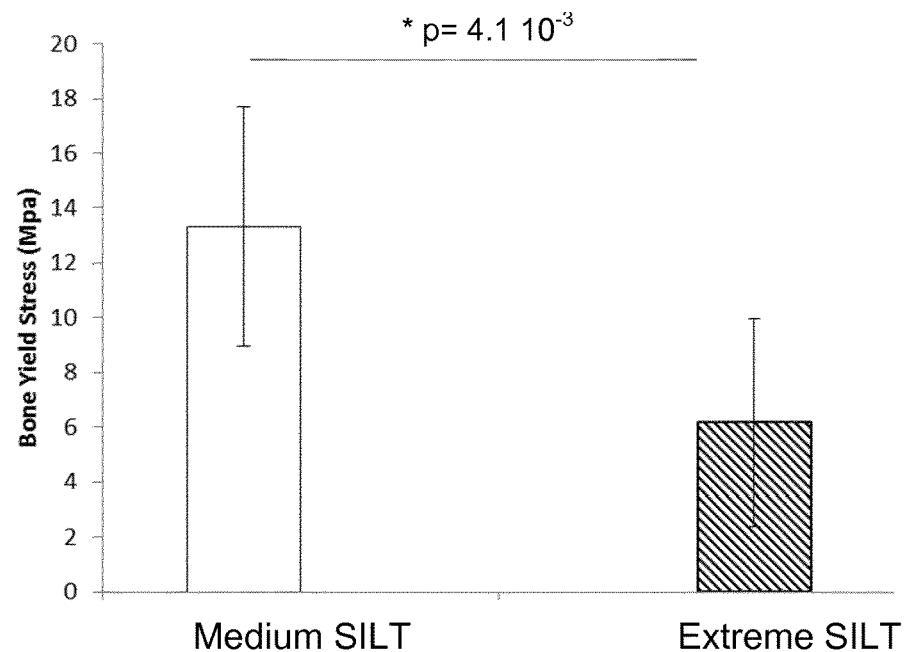
FIG. 5. Application of the quantitative process on the determination of quality of the bone Patients have been classified in two groups "stage 1" presenting medium values of SILT; and "stage 2" presenting extreme values of SILT. The corresponding bone samples, issued from each patient, have been assessed for the bone yield stress (A) and for Young's modulus (B).
Figure 5:
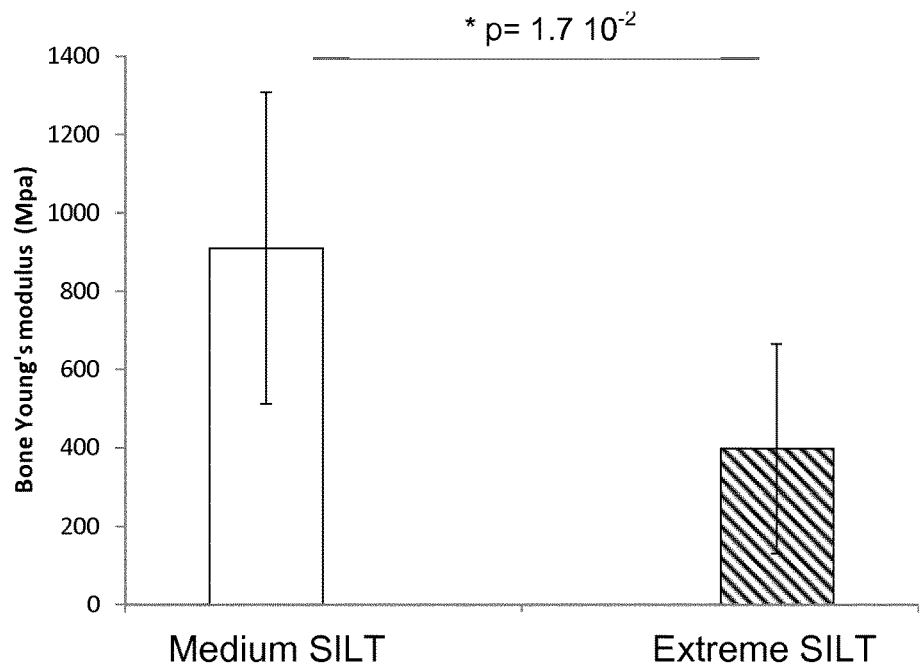

As presented in example 2, for each group the mean value of the bone yield stress was calculated and is presented in FIG. 5A:

For patients with medium SILT (stage 1), the bone yield stress mean is 13.35+/−4.3 MPa.

For patients with extreme SILT (stage 2), the bone yield stress mean is 6.18+/−3.8 MPa.

As shown in FIG. 5A, a relevant difference in bone yield stress is noted between both groups, according to the statistical test of Mann-Withney (p=4.1 $10^{-3}$).

FIG. 5B shows the mean of each group for the Young's modulus, another marker of the solidity of the bones.

Results for each group are presented in the following table 2:

TABLE 2

Young's modulus mean for each group of patients

| | Young's modulus (MPa) |
|---|---|
| Medium SILT | 910 +/− 398 |
| Extreme SILT | 535 +/− 267 |
| p-value | 0.017 |

Example 4. Application of the Process of the Invention on the Determination of the Dermis Quality Samples of dermis of 5×5 mm have been prelevated from each of the 34 patients as presented in example 1, during the hip surgery intervention.

The aim of the clinical study was to identify, if any, a relation between the forearm surface microrelief, obtained as presented in examples 2 and 3, and the quality of dermis.

These 34 patients have been categorized in two groups, based on one of the following classification method:

Visual classification of their cutaneous replica as presented in example 2, and

Measure of their SILT values, as presented in example 3.

In parallel, the 34 samples of dermis have been assessed to evaluate the elastin/collagen ratio by biphotonic confocal microscopy as presented in (Czekalla et al., 2017).

Briefly, the dermis samples of all patients were observed by biphotonic confocal imaging (A1RMP PLUS®, Nikon) using an excitation wavelength of 850 nm. Second harmonic generated light from collagen and autofluorescent light from elastin were collected on two channels with specific band-pass filters of 400-490 and 500-550 nm, respectively. A 25×, 1.1-NA water immersion objective (CFI Apo LWD 25XW; Nikon) was used. The image field of view was 512×512 µm$^2$ with a resolution of 0.5 µm. To scan the thickness of the dermis, stacks of 2D images were recorded in each area, with a time scan of 2 s and an average of two scans per image, every 1 µm in depth.

For each sample, obtained pictures for elastin and collagen were treated with the software ImageJ 1.47 v (NIH, USA). A pixels number was obtained for collagen (Npix_col) and elastin (Npix_ela) and the ratio elastin/collagen was calculated according to the following equation:

$$R\ E/C = Npix\_ela/Npix\_col \quad \text{Equation 4}$$

Results are presented in table 3 below:

TABLE 3

Values of SILT and visual stage of cutaneous replica, and E/C ratio for each sample of dermis

| Patient | SILT | Stage (according to SILT value) | Stage (visual) | Correlation visual/SILT | RE/C Elastin collagen ratio |
|---|---|---|---|---|---|
| P1 | 64 | 1 | 1 | YES | 0.019 |
| P2 | 82 | 1 | 1 | YES | 0.039 |
| P3 | 42 | 2 | 2 | YES | 0.038 |
| P4 | 121 | 2 | 2 | YES | 0.038 |
| P5 | 37 | 2 | 2 | YES | 0.058 |
| P6 | 60 | 1 | 1 | YES | 0.039 |
| P7 | 66 | 1 | 2 | NO | 0.051 |
| P8 | 117 | 1 | Not done | | 0.011 |
| P9 | 77 | 1 | 1 | YES | 0.027 |
| P10 | 31 | 2 | 2 | YES | 0.063 |
| P11 | 54 | 1 | 1 | YES | 0.072 |
| P12 | 70 | 1 | 1 | YES | 0.008 |
| P13 | 69 | 1 | 2 | NO | 0.038 |
| P14 | 167 | 2 | Not done | | 0.149 |
| P15 | 70 | 1 | 2 | NO | 0.016 |
| P16 | 56 | 1 | 1 | YES | 0.017 |
| P17 | 131 | 2 | 2 | YES | 0.037 |
| P18 | 248 | 2 | 2 | YES | 0.087 |
| P19 | 52 | 1 | 1 | YES | 0.006 |
| P20 | 67 | 1 | 2 | NO | 0.034 |
| P21 | 129 | 2 | 2 | YES | 0.106 |
| P22 | 93 | 1 | 2 | NO | 0.011 |
| P23 | 45 | 1 | 1 | YES | 0.010 |
| P24 | 97 | 1 | 1 | YES | 0.017 |
| P25 | 157 | 2 | 2 | YES | 0.011 |
| P26 | 57 | 1 | 1 | YES | 0.028 |
| P27 | 114 | 1 | 1 | YES | 0.019 |
| P28 | 58 | 1 | 1 | YES | 0.006 |
| P29 | 118 | 1 | 1 | YES | 0.011 |
| P30 | 49 | 1 | 1 | YES | 0.013 |
| P31 | 117 | 1 | 2 | NO | 0.006 |
| P32 | 92 | 1 | 1 | YES | 0.010 |
| P33 | 67 | 1 | 1 | YES | 0.016 |
| P34 | 74 | 1 | 1 | YES | 0.021 |

Based on this categorization of patients, the mean value of the elastin/collagen ratio was calculated for each group, and is presented in FIGS. 6A and 6B.

FIG. 6A represents the mean value of patients from groups 1 and 2, defined after visual classification of cutaneous replica of each patient:

the group "stage 1" also designated as "great visual" comprises 18 patients; the average elastin/collagen ratio value for this group is 0.021+/−0.016;

the group "stage 2" also designated as "low visual" comprises 14 patients; the average elastin/collagen ratio value for this group is 0.041+/−0.028.

The difference in elastin/collagen ratio between these two groups, according to the statistical test of Mann-Withney, is significant (p value=0.033).

FIG. 6B represents the mean value of patients from groups 1 and 2, defined according to the SILT values of cutaneous replica of each patient:

the group "stage 1" also designated as "medium SILT" comprises 25 patients; the average elastin/collagen ratio value for this group is 0.022+/−0.015;

the group "stage 2" also designated as "extreme SILT" comprises 9 patients; the average elastin/collagen ratio value for this group is 0.065+/−0.039.

The difference in Elastin/Collagen ratio between these two groups, according to the statistical test of Mann-Withney, is very significant (p value=0.00098).

Among the 9 patients that were classified as having "extreme SILT", four of them present a high ratio E/C (patients P10, P14, P18 and P21), characteristic of a low quality skin. Five of them present a "medium" E/C ratio, comprised between 0.037 and 0.058; and only one of them has a low ratio E/C (P25).

Remarkably, among the 25 patients that were classified as "stage 1" on the basis of their SILT values, and therefore identified according to the process of the invention as presenting a good quality of dermis, the ratio E/C is inferior to a value of 0.040 in almost all cases, except for the only patient P11.

The two isolated cases (P11 and P25) that do not match with the expected values of ratio E/C should be tested with another technique enabling the evaluation of the quality of dermis.

As for the evaluation of bone quality, the classification based on SILT values give more discriminating results than the visual classification of patients based on cutaneous replica pictures. However, the visual classification presents the advantage to be performed in a shorter time, with minimal equipment, if necessary on the bedside of the patient.

REFERENCES

Patents

WO 2005/122893
WO 2013/076579
WO 02/095475
WO 03/001268

Scientific Literature

Sullivan K J, Husak L E, Altebarmakian M, Brox W T. *Demographic factors in hip fracture incidence and mortality rates in California*, 2000-2011. J Orthop Surg Res. 2016 Jan. 8; 11:4.

Vochteloo A J, Borger van der Burg B L, Röling M A, van Leeuwen D H, van den Berg P, Niggebrugge A H, de Vries M R, Tuinebreijer W E, Bloem R M, Nelissen R G, Pilot P. *Contralateral hip fractures and other osteoporosis-related fractures in hip fracture patients: incidence and risk factors. An observational cohort study of 1,229 patients.* Arch Orthop Trauma Surg. 2012 August; 132(8):1191-7

Aurégan J C, Frison A, Bégué T, Hannouche D, Bosser C, Bensidhoum M, Hoc T. *Contralateral hip fracture in the elderly: are decreased body mass index and skin thickness predictive factors?* Int Orthop. 2017 February; 41(2):247-252

Czekalla C, Schönborn K H, Döge N, Jung S, Darvin M E, Lademann J, Meinke M C. *Impact of Body Site, Age, and Gender on the Collagen/Elastin Index by Noninvasive in vivo Vertical Two-Photon Microscopy.* Skin Pharmacol Physiol. 2017; 30(5):260-267.

Sampson J. *A method of replicating dry or moist surfaces for examination by light microscopy.* Nature. 1961 Aug. 26; 191:932-3.

Hashimoto K. *New methods for surface ultrastructure: Comparative studies of scanning electron microscopy, transmission electron microscopy and replica method.* Int J Dermatol. 1974 November-December; 13(6):357-81.

Bérot, M, Auregan, J C, Imbert, L, et al. *Mechanics of osteoporotic trabecular bone.* Mécanique et industries, 2012, vol. 13, no 6, p. 373-380.

The invention claimed is:

1. A non-invasive process for evaluating the quality of one or more dense connective tissue(s) in a patient, comprising the following steps:
   a) analyzing the profile of the microrelief of a cutaneous replica of a portion of the skin of said patient by determining, on picture(s) of said cutaneous replica, the roughness index (Ra) of the microrelief with an optical sensor, wherein the roughness index (Ra) is defined as the distance of the line at the surface of the replica to the mean line profile, and is calculated according to the following equation: $Ra = 1/N \Sigma_{i=1}^{N} |Zi|$
   where N corresponds to the collected points along the measurement direction, and for each point (i), Zi corresponds to the distance in the vertical direction between the surface of the replica and the mean line profile;
   b) identifying cutaneous replica of stage 1, representative of healthy skins, and cutaneous replica of stage 2 representative of altered skins, a cutaneous replica of stage 2 being indicative of low quality of the one or more dense connective tissue(s) in the patient's body, wherein step a) comprises the quantification of the roughness indexes measured in two directions of the replica picture, longitudinal (0°) and transversal (90°), wherein the values of both roughness indexes measured on each direction are added up to obtain a value of Skin Index of Living Tissues (SILT), wherein the SILT value is compared to reference value(s) to be classified as "medium SILT value" or "extreme SILT value", and wherein a cutaneous replica of stage 1 is defined as having a medium SILT value, and a cutaneous replica of stage 2 is defined as having an extreme SILT value.

2. The process according to claim 1, wherein a cutaneous replica of stage 1 is defined as having a medium SILT value, comprised between 45 μm and 120 μm, and a cutaneous replica of stage 2 is defined as having an extreme SILT value, strictly inferior to 45 μm or strictly superior to 120 μm.

3. The process according to claim 1, wherein the dense connective tissue is bone tissue.

4. The process according to claim 3, wherein the non-invasive process is used for determining the risk of occurrence of a contralateral hip fracture in a patient.

5. The process according to claim 1, wherein the dense connective tissue is dermis.

6. The process according to claim 1, wherein the patient is an elderly person.

7. The process according to claim 1, wherein the cutaneous replica is obtained by application on a portion of the skin of the patient of a silicone polymer.

8. The process according to claim 1, wherein the non-invasive process is used for following over time the quality of one or more dense connective tissue(s) in a patient.

9. The process according to claim 1, wherein its implementation involves the use of:
   (1) a diagnostic kit comprising:
      means for obtaining a cutaneous replica of a patient, including silicone polymer and a molding apparatus, and
      at least two reference pictures of reference cutaneous replica, one being representative of the stage 1 and the other one being representative of the stage 2, as defined in claim 6;
   (2) a camera; and
   (3) optic fibers.

10. A diagnostic kit comprising:
   means for obtaining a cutaneous replica of a patient, including silicone polymer and a molding apparatus, and
   at least two reference pictures of reference cutaneous replica, one being representative of the stage 1 and the other one being representative of the stage 2, as defined in claim 2.

* * * * *